(12) United States Patent
Harpas et al.

(10) Patent No.: US 8,273,030 B2
(45) Date of Patent: Sep. 25, 2012

(54) METHOD OF ESTIMATING PULSE WAVE VELOCITY

(75) Inventors: Peter Chris Harpas, Chipping Norton (AU); Ahmad M. Qasem, Merrylands (AU)

(73) Assignee: Atcor Medical Pty Ltd, New South Wales (AU)

(*) Notice: Subject to any disclaimer, the term of this patent is extended or adjusted under 35 U.S.C. 154(b) by 1082 days.

(21) Appl. No.: 12/095,898

(22) PCT Filed: Nov. 27, 2006

(86) PCT No.: PCT/AU2006/001789
§ 371 (c)(1),
(2), (4) Date: Jul. 8, 2008

(87) PCT Pub. No.: WO2007/062456
PCT Pub. Date: Jun. 7, 2007

(65) Prior Publication Data
US 2009/0030328 A1    Jan. 29, 2009

(30) Foreign Application Priority Data
Dec. 1, 2005 (AU) ................................ 2005906748

(51) Int. Cl.
*A61B 5/02* (2006.01)
*A61B 5/00* (2006.01)
*A61B 8/00* (2006.01)

(52) U.S. Cl. .................. 600/485; 600/301; 600/438

(58) Field of Classification Search ................. None
See application file for complete search history.

(56) References Cited

U.S. PATENT DOCUMENTS

| 5,265,011 | A   | 11/1993 | O'Rourke |
| 6,428,482 | B1  | 8/2002  | Sunagawa et al. |
| 6,740,045 | B2  | 5/2004  | Amano |
| 7,935,062 | B2* | 5/2011  | Karamanoglu et al. ...... 600/504 |

OTHER PUBLICATIONS

Rogers, Age-Associated Changes in Regional Aortic Pulse Wave Velocity, Journal of the American College of Cardiology, vol. 38, No. 4, 2001.*
Kelly et al., Noninvasive determination of age-related changes in the human arterial pulse, Circulation 1989, 80:1652-1659.*
Murgo et al., Aortic input impedance in normal man: relationship to pressure wave forms, Circulation 1980, 62:105-116.*

(Continued)

*Primary Examiner* — James Ketter
*Assistant Examiner* — Reza Ghafoorian
(74) *Attorney, Agent, or Firm* — Marshall, Gerstein & Borun LLP (57) ABSTRACT

A method of estimating blood pressure Pulse Wave Velocity (PWV) in the aorta from a recording of a pressure waveform at a single site. The method comprises the following steps: 1. measuring the patient's arterial pressure relative to time in order to estimate a central pressure waveform (CPW); 2. estimating the patient's aortic pressure pulse transit time (PPTT) from the CPW; 3. estimating the patient's carotid to femoral arterial distance from the patient's physical characteristics; and 4. dividing the patient's estimated carotid to femoral arterial distance by the patient's estimated PPTT to estimate the patient's PWV.

16 Claims, 7 Drawing Sheets

OTHER PUBLICATIONS

Wilkinson et al., Changes in the derived central pressure waveform and pulse pressure in response to angiotensin II and noradrenaline in man, Journal of Physiology (2001), 530.3, pp. 541-550.*

Food and Drug Administration: 510K Summary for SphygmoCor Px Regulation No. 21CFR870,1110 (K012487). Rockville, MD, Food and Drug Administration, Department of Health and Human Services, 2002.*

Blacher et al., Aortic Pulse Wave Velocity as a Marker of Cardiovascular Risk in Hypertensive patients, Hypertension 1999, 33:1111-1117.*

International Search Report for International Application No. PCT/AU2006/001789 dated Mar. 8, 2007.

Stergiopulos et al., "Physical basis of pressure transfer from periphery to aorta: a model-based study", *Am. J. Physiol. Heart Circ. Physiol.*, vol. 274, pp. 1386-1392 (Apr. 1998).

* cited by examiner

Fig_2.

METHOD OF ESTIMATING PULSE WAVE VELOCITY

FIELD OF THE INVENTION

The present invention relates to a method of estimating blood pressure Pulse Wave Velocity (PWV) in the aorta from a recording of a pressure waveform at a single site.

BACKGROUND OF THE INVENTION

Arterial stiffness is a major mechanism by which cardiovascular disease drives cardiovascular risk. Increases in arterial stiffness in the arterial tree increases central systolic and pulse pressure, and load on the left ventricle, and decreases the perfusion pressure through the coronary arteries in diastole, thereby increasing the risk of heart attacks, heart failure and stroke.

PWV is a well-established technique for obtaining a measure of arterial stiffness in a section of artery between two locations in the arterial tree. The velocity of the pulse wave along an artery is dependent on the stiffness of that length of artery. Most commonly, PWV is measured between the carotid and femoral peripheral artery sites in order to provide a measure predominantly of arterial stiffness of the aorta. Aortic PWV increases with age, typically doubling between the ages of 30 and 60.

As living standards improve, the incidence of diseases that are closely affected by lifestyle, such as hypertension, obesity, diabetes and hyperlipidemia, progressively increase. Arteriosclerosis, due to abnormalities or degeneration of the arterial wall, is known to be a major complication that is associated with these diseases and one that can lead to cardiovascular events such as heart failure, heart attacks and stroke. As a result, cardiovascular disease and stroke are the leading cause of mortality and morbidity in industrialised nations. With these numbers increasing, the need for better early detection and treatment of cardiovascular disease is becoming a clinical priority. Historically, healthcare professionals focused primarily on treating patients who showed evidence of these diseases. For early detection and intervention to be successful, "at risk" patients who are still asymptomatic will need to be identified. Assessment and treatment of cardiovascular risk will not only delay the onset of the disease, but also reduce healthcare costs and improve quality of life.

PWV is considered the "gold standard" by clinicians for measuring arterial stiffness. In clinical studies the following findings have been reported and widely acknowledged:

PWV is suggested as a marker of arteriosclerotic load or cardiovascular risk;
   Aortic PWV correlates with the severity of independently assessed diabetic complications;
   Arterial stiffness increases with age and in subjects with hypertension, diabetes mellitus, atherosclerosis, and end-stage renal disease;
   Aortic PWV is strongly associated with the presence and extent of atherosclerosis and with aortic structural breakdown and constitutes a forceful marker and predictor of cardiovascular risk in hypertensive patients; and
   Aortic PWV is a strong independent predictor of cardiovascular and all-cause mortality in patients with end-stage renal disease on hemodialysis.

Accordingly, aortic stiffness measurements are an important tool in identifying patients at high risk of the effects of cardiovascular disease. The ability to identify these patients leads to better risk stratification and earlier and more cost-effective preventive therapy.

A known system used to measure PWV is the Applicant's SphygmoCor PVx (Trade Mark) Pulse Wave Velocity system, which, in pulse wave velocity mode, measures the velocity of the blood pressure waveform between any two superficial artery sites. This system uses simultaneous measurements of a single-lead ECG and with a tonometer (pressure sensor) of the pressure pulse waveform sequentially in the two peripheral artery sites (e.g. carotid & femoral). This device has automated software analysis and database facilities and its simplicity of use makes it suited for physician's offices. Only one operator is required to use this system. However, this system requires two sequential measurements to be performed using the R-wave peak of the ECG as the intermediate time reference point, and as such is relatively time consuming and slightly invasive to the patient.

Another known PWV system is the Artech Medical Complior (Trade Mark) system, which uses simultaneous direct contact pressure pulse sensors applied to major arterial sites without the need for an ECG. This allows a simultaneous recording of the same pulse wave as it transits through the body, and then calculates the PWV, heart rate and pulse transit times. A disadvantage of this system is it uses a cross correlation algorithm that is prone to errors due to differing wave shapes at the two arterial sites.

Another known system is the Colin Medical, COLIN Vascular Profile VP-1000 (trade mark) system, which is a screening device for the non-invasive assessment of arteriosclerosis. This system uses "Waveform Analysis and Vascular Evaluation" WAVE (Trade Mark), technology and assesses arteries by PWV and ABI (Ankle Brachial Index). The two indices are obtained using simultaneous blood pressure and waveform measurements on all four limbs along with ECG and phonocardiogram tracings. Disadvantages of this system are it is expensive and bulky and incorporates a large distance correction for the upper and lower limbs as the pulse travels in opposite directions.

OBJECT OF THE INVENTION

It is the object of the present invention to overcome or substantially ameliorate one or more of the above disadvantages.

SUMMARY OF THE INVENTION

Accordingly, in a first aspect, the present invention provides a method of estimating blood pressure Pulse Wave Velocity (PWV) in the aorta from a recording of a pressure waveform at a single site, the method comprising the following steps:

1. measuring the patient's arterial pressure relative to time in order to estimate a central pressure waveform (CPW);
   2. estimating the patient's aortic pressure pulse transit time (PPTT) from the CPW;
   3. estimating the patient's carotid to femoral arterial distance from the patient's physical characteristics; and
   4. dividing the patient's estimated carotid to femoral arterial distance by the patient's estimated PPTT to estimate the patient's PWV.

The patient's single site pressure measurement is preferably taken non-invasively, most preferably using the Applicant's SphygmoCor Px (Trade Mark) Pulse Wave Analysis system, In a preferred form, the patient's radial artery pressure is measured, which is then used to derive the patient's central pressure waveform (CPW). In another form, the patient's carotid artery pressure is measured and used as an approximation of the CPW.

The patient's carotid to femoral arterial distance is preferably estimated from the patient's height, weight and body mass index (BMI). Alternatively, a direct measurement of the distance between the carotid and femoral artery can be made, or the path length can be estimated from superficial body surface measurements.

The patient's aortic PPTT is preferably estimated from the patient's CPW by estimating incident pressure waveform (IPW) and reflected pressure waveform (RPW) components of the patient's CPW, whereby the patient's aortic PPTT has a linear relationship with the time difference between the foot of the IPW and the foot of the RPW.

The aortic pressure pulse transit time (PPTT), and both the IPW and RPW components, are preferably calculated non-invasively from an ascending aortic pressure waveform (CPW) measurement that is derived using the Applicant's SphygmoCor Px (Trade Mark) Pulse Wave Analysis system. To decompose the CPW into the IPW and the RPW components, a triangular flow waveform (FL) is estimated from zero at the time of the foot of the CPW up to the first systolic peak (T1) in the CPW, which corresponds to the time of peak flow, and then back to zero at the time of the closure of the aortic valve, which is estimated as the ejection duration (ED) from the CPW. The height of the estimated triangular flow waveform (FL) is arbitrary. The Characteristic Impedance (Zc) is then calculated using the ratio of the Fast Fourier Transform (FFT) of both CPW and the estimate triangular flow waveform (FL). The characteristic impedance (Zc) is needed to derive the IPW and the RPW, based upon an arterial wave reflection model which utilises CPW, Zc and the estimated triangular flow waveform (FL) as input parameters.

However, using the estimated triangular flow waveform (FL) yields physiological unrealistic waveforms of the IPW and the RPW. To improve this, three conditions are imposed: RPW is constant until at least T1; there is no reflection in the IPW after T1; and the beginning of RPW is smoothed using spline interpolation. This second stage of processing results in the (improved) estimated flow waveform ($FL_{imp}$), the IPW and the RPW being smoother and more physiologically representative than that resulting from the initial (assumption-based) calculation. The estimated PPTT is then calculated as the time between the foot of the IPW and the RPW, or by using a cross correlation algorithm for increased accuracy. A regression equation is used to convert the estimated PPTT into representing the carotid-femoral transit time, based on analysis of a database containing SphygmoCor Pulse Wave Velocity and SphygmoCor Pulse Wave Analysis measurements for the same patients at the same time. The patient's carotid-femoral PWV is then calculated by dividing the arterial distance by the carotid-femoral transit time.

The carotid-femoral PWV is then calculated from the IPW and the RPW components of the patient's CPW, most preferably estimated using the following steps:

1. measuring the time from the foot of the CPW to the first systolic peak (T1);
2. measuring the time from the foot of the CPW to the closure of the aortic valve, which represents the ejection duration (ED);
3. estimating a triangular flow waveform (FL) assuming zero flow at the foot of the IPW, peak flow at T1 and zero flow again at ED;
4. calculating a Fast Fourier Transform (FFT) of both CPW and the estimated triangular flow waveform (FL) to determine the impendence magnitude (Z) using the following formula:

$Z = FFT(CPW)/FFT(FL)$;

5. calculating the characteristic impedance Zc as the average of the $4^{th}$ to $7^{th}$ harmonics;
6. calculating the IPW (forward) pressure waveform function ($P_f(t)$) using the following equation:

$P_f(t) = [CPW(t) + ZcFl(t)]/2$;

7. calculating the RPW (backward) pressure waveform function ($P_b(t)$) is calculated using the following equation:

$P_b(t) = [CPW(t) - ZcFl(t)]/2$ 8. calculating the max dp/dt of the $P_b$ and locating the intersection of the upstroke slope with the baseline to initially estimate the start (Ti) of the reflected wave;
9. making pressure values before Ti equal to the baseline pressure in $P_b$ and calculating a new estimate of Pb and Pf (Pb1 and Pf1) using the following formulas:

$P_{b1}(0 \ldots T_i) = P_b(0)$ $P_{b1}(T_i + T_s \ldots T) = P_b(T_i + T_s \ldots T)$ $P_{f1}(0 \ldots T_i) = P_f(0 \ldots T_i) + (P_b(0 \ldots T_i) - P_{b1}(0 \ldots T_i))$ $P_{f1}(T_i + T_s \ldots T) = P_f(T_i + T_s \ldots T)$ where $T_s$ = sampling period and T = cardiac period.
10. calculating a new estimate of the forward wave ($P_{f2}$) by smoothing the peak of the wave to ED using spline interpolation;
11. calculating a new estimate of $P_b$ ($P_{b2}$) using the following equation:

$P_{b2}(T_{peak} \ldots ED) = P_{b1}(T_{peak} \ldots ED) + (P_{f1}(T_{peak} \ldots ED) - P_{f2}(T_{peak} \ldots ED))$ where $T_{peak}$ = Time at the peak of the forward wave.
12. calculating the (improved) estimated flow waveform ($FL_{imp}$) from $P_{b2}$ and $P_{f2}$ using the following equation:

$FL_{imp} = (2 \times P_{f2}) - CPW = (2 \times P_{b2}) + CPW$ 13. if any pressure value of $P_{b2}$ before ED is less than the baseline pressure then reduce $T_1$ by one sampling point and repeat steps 3 to 12. If not continue to the next step;
14. re-calibrating $P_{b2}$ and $P_{f2}$ so both have the same height and calculate cross correlation, wherein the time of the highest correlation is the estimated aortic PPTT;
15. converting the estimated aortic PPTT to carotid femoral PPTT using a linear regression equation;
16. calculating carotid to femoral distance from direct external measurement, or automatically from height and weight or BMI; and
17. determining the carotid-femoral PWV by dividing the carotid to femoral distance by the carotid-femoral PPTT.

BRIEF DESCRIPTION OF THE DRAWINGS

A preferred form of the present invention will now be described, by way of an example only, with reference to the accompanying drawings, wherein.

DETAILED DESCRIPTION OF THE PREFERRED EMBODIMENTS

Figure 1A:
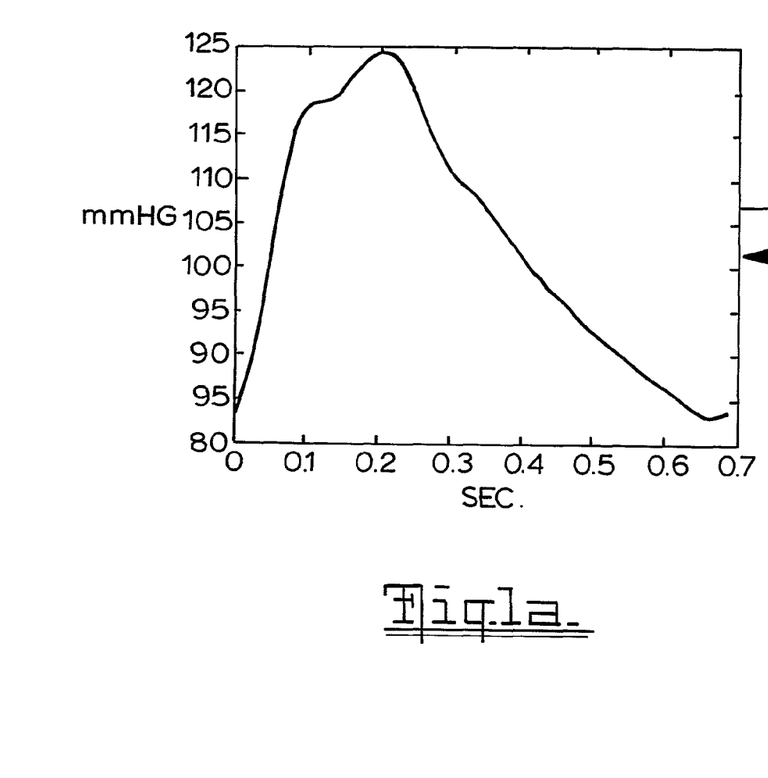
FIG. 1a is a plot of central pressure waveform (CPW) versus time.
Figure 1B:
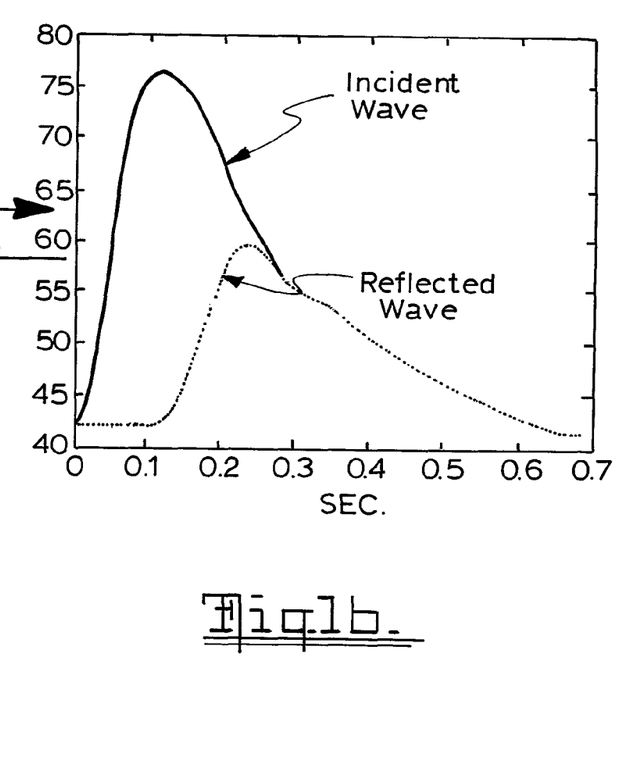
FIG. 1b is a decomposition of the plot shown in FIG. 1a into incident and reflected pressure waveforms.

FIG. 1a shows an ascending aortic pressure waveform. FIG. 1b shows the deconstruction of the pressure wave into two components: the Incident Wave, which is related to left ventricular activities as a result of the heart's contraction; and the backward or Reflected Wave, which is related to, and mainly reflects, arterial elastic properties.

This deconstruction provides a better understanding of the interaction between cardiac and vascular activities and allows for waveform features to be directly related to either cardiac or vascular activity.

An embodiment of the present invention will now be described which allows measurement of the time of the arrival of the reflected wave back at the heart, which is known to be related to the aortic PWV. More particularly, the embodiment allows the incident and reflected waves to be calculated non-invasively from parameters available from the Applicant's SphygmoCor Vx (Trade Mark) Pulse Wave Velocity system, in pulse wave analysis mode. The features from these waves relate to aortic pulse wave velocity (PWV) or to aortic arterial stiffness directly.

Figure 11:
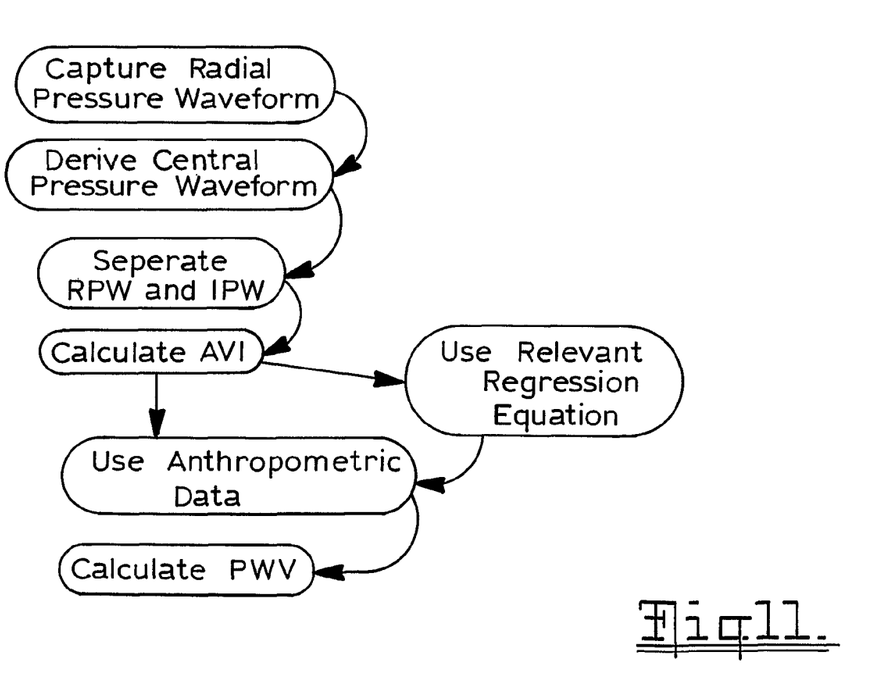
FIG. 11 is a basic flow chart of an embodiment of a method of estimating PWV according to the invention.

The general steps in an embodiment of the method a method of estimating PWV from a single site pressure measurement of a patient are shown in FIG. 11 and are as follows.

Firstly, to estimate the aortic pressure transit time, both incident and reflected pressure waveforms (IPW and RPW) are calculated from a non-invasive central pressure waveform (CPW) measurement that is taken using the Applicant's SphygmoCor Vx (Trade Mark) Pulse Wave Velocity system, in Pulse Wave Analysis mode. To decompose the waveforms, an estimated triangular flow waveform (FL) is needed. This is estimated by using the time from the foot of the wave to the first systolic peak (T1), which corresponds to the time of peak flow, and the time from the foot of the wave to the closure of the aortic valve, which represents the ejection duration (ED) from the CPW. The height of the estimated triangular flow waveform (FL) is arbitrary.

The Characteristic impedance (Zc) is then calculated using the ratio of the Fast Fourier Transform (FFT) of both the CPW and the estimated triangular flow waveform (FL). The characteristic impedance (Zc) is needed to derive the IPW and the RPW components. However, using the triangular estimation of flow yields unrealistic physiological waveforms of the IPW and the RPW components. To improve this, three conditions are imposed:

1. the RPW is constant until at least T1;
2. there is no reflection in the IPW after T1; and
3. the beginning of the RPW is smoothed using spline interpolation.

This processing results in the (improved) estimated flow waveform ($FL_{imp}$), the IPW and the RPW being smoother and more physiologically representative than that resulting from the initial calculations.

The estimated PPTT is then calculated as the time between the foot of the IPW and the RPW using a cross correlation algorithm for increased accuracy. A regression equation is used to convert the estimated PPTT to represent the carotid-femoral transit time from an analysis of database containing SphygmoCor Pulse Wave Velocity and SphygmoCor Pulse Wave Analysis measurements for the same patients at the same time).

The arterial distance (carotid-femoral) is either estimated externally by direct measurement, or estimated from using the patient's height and weight or BMI (body mass index). The patient's carotid-femoral PWV is then calculated by dividing the arterial distance by the carotid-femoral PPTT. It should be appreciated that the algorithm calculates transmission time of the reflected wave without using a flow measurement. It only requires an estimated triangular flow waveform. The algorithm with its signal processing decomposes the central waveform into smoother and more physiologically realistic forward (incident) and backward (reflected) waves than the cruder results of the initial calculation. The flow waveform calculated from the results of the algorithm, approximates real flow waveforms. To calculate PWV, the algorithm only requires the time of the first systolic peak and the time of the end of systole calculated from the CPW. The use of combination of cubic spline interpolation, derivative and cross correlation is used to calculate aortic PWV from non-invasive central pressure waveform. The assumptions made in the algorithm about reflected and incident waves, improves the detection of aortic transmission time. If the time of the first systolic peak (T1) was not located accurately, the algorithm using iterative method would adjust the time of the peak of the forward wave until it reach physiologically acceptable flow, backward and forward waveforms.

Figure 10:
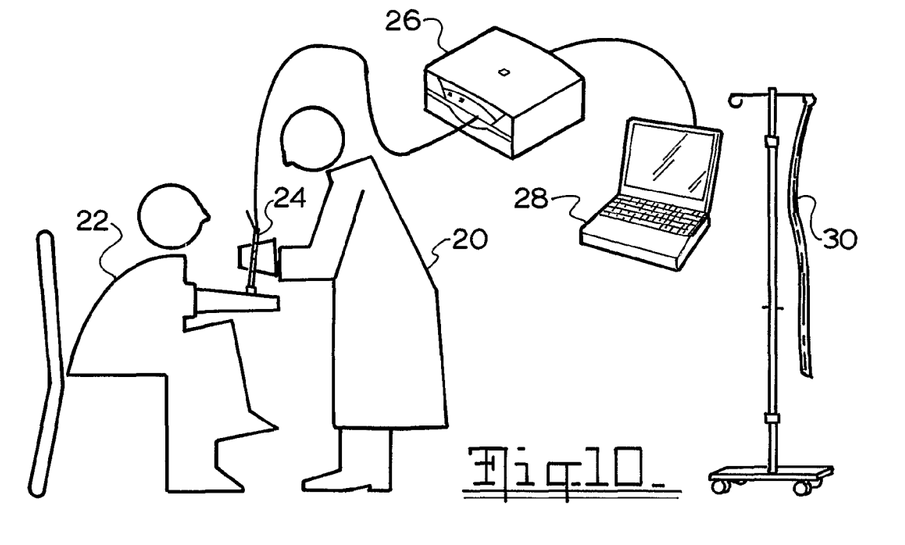
FIG. 10 is a schematic diagram of an embodiment of a device used to estimate PWV according to the invention.

The embodiment will now be described in more detail. Firstly, a non-invasive central pressure waveform (CPW) measurement, an example of which is shown in FIG. 1a, is taken using the Applicant's SphygmoCor Vx (Trade Mark) Pulse Wave Velocity system. This system, in pulse wave analysis mode, measures the patient's radial pressure waveform (RPW) and derives the patient's CPW, as will be described below. FIG. 10 shows an example of equipment used by a physician 20 to measure CPW in a patient 22, namely: a pressure sensor 24; an electronics module 26; a computer (with software) 28 and a tape measure 30. The sensor 24 is connected to the module 26 which is in turn connected to the computer 28.

The measurement process involves the physician 20 taking anthropometric measurements of the patient 22, including: height, weight and the distance between the carotid artery and femoral artery locations with the tape measure 30. Once these details have been saved to the computer 28, the physician 20 places the pressure sensor 24 onto the radial artery of the patient 22 and observes the radial pressure waveform on the screen of the computer 28. The radial pressure waveform should appear physiologically correct with a consistent pulse height and a horizontal baseline. Once 10 seconds of valid data has been observed the physician 20 captures and records this radial pressure waveform data to the computer 28. The software in the computer 28 then derives the CPW from the measured data, as shown in FIG. 1a.

Both incident and reflected pressure waveforms (IPW and RPW), as shown in FIG. 1b, are then calculated from the CPW measurement, as is described below.

Figure 2:
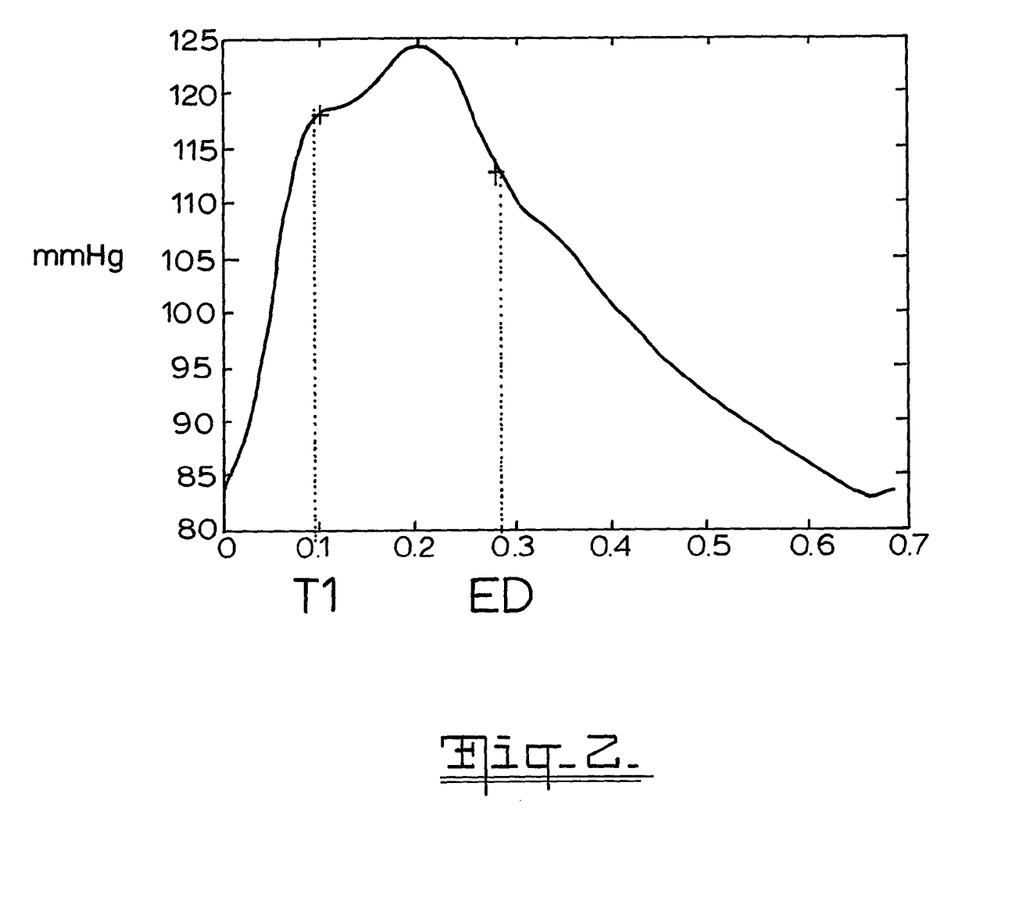
FIG. 2 is a CPW of FIG. 1a showing time of the first systolic peak (T1) and time of the end of ejection (ED)
Figure 3:
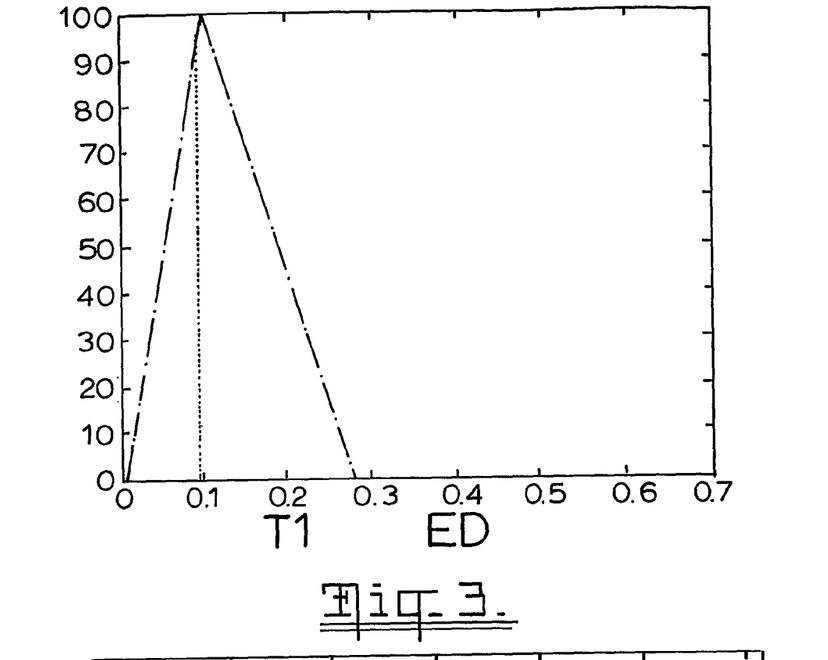
FIG. 3 is a simulated triangular waveform based on the T1 and ED shown in FIG. 2.

Firstly, to decompose the waveforms, a triangular flow waveform (FL) (see FIG. 3) is estimated by using the time from the foot of the wave to the first systolic peak (T1), which corresponds to the time of peak flow, and the time from the foot of the wave to the closure of the aortic valve, which represents the ejection duration (ED) from the CPW (see FIG. 2). The height of the waveform is arbitrary as it will not affect the calculation.

Figure 4:
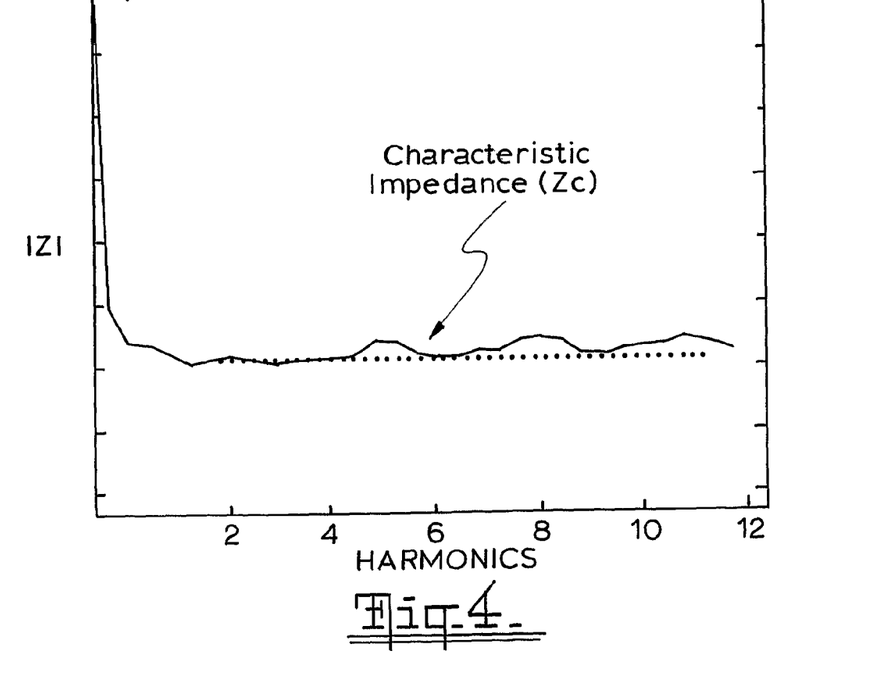
FIG. 4 is a plot of impedance modulus with estimated value of characteristic impedance.

Fast Fourier Transform (FFT) of both CPW and the estimated triangular flow waveform (Fl) is then calculated and used to find the impedance magnitude (|Z|) using the following $$|Z| = \frac{|FFT(CPW)|}{|FFT(Fl)|}$$

formula:

The |Z| will be high at lower harmonics but then stabilize after $3^{rd}$ or $4^{th}$ harmonics (see FIG. 4). The characteristic impedance ($Z_c$) will be calculated as the |Z| average of the $4^{th}$ to the $7^{th}$ harmonics.

Figure 5:
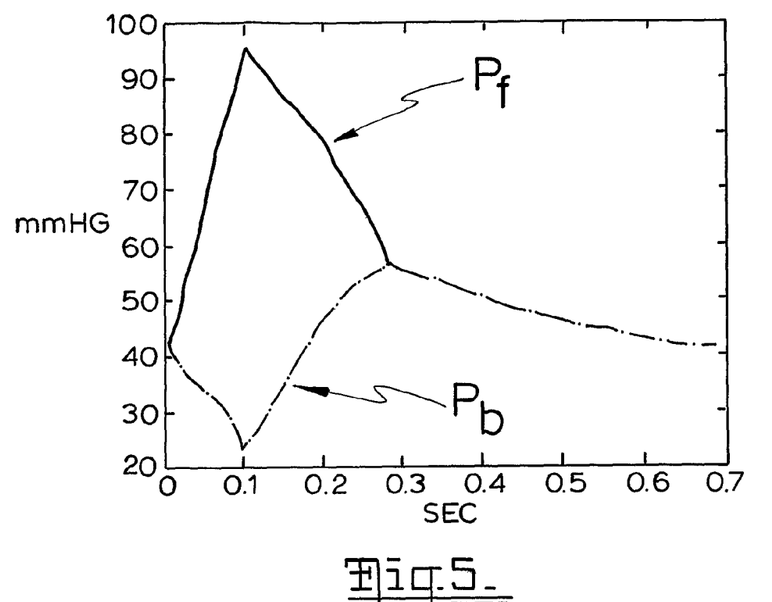
FIG. 5 is a plot of initial estimated forward and backward pressure.

The incident (forward) and reflected (backward) pressure waveforms ($P_f$ and $P_b$) are then calculated using the following equations. An example of the result is shown in FIG. 5.

$$P_f(t) = \frac{CPW(t) + Z_C Fl(t)}{2}$$

$$P_b(t) = \frac{CPW(t) - Z_C Fl(t)}{2}$$

Figure 6:
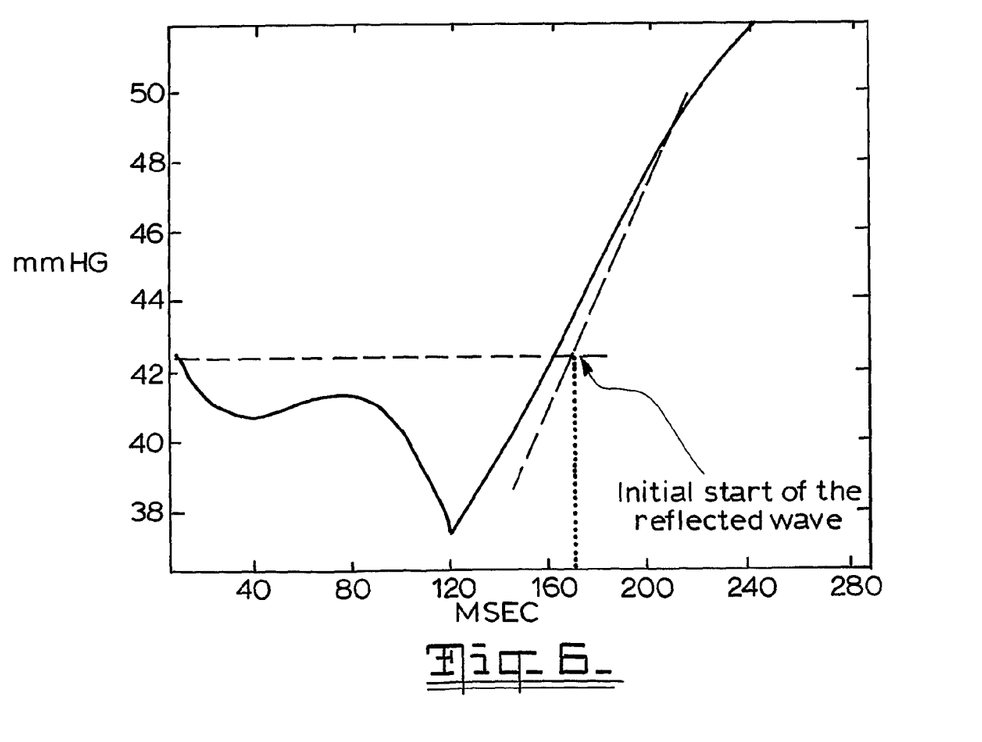
FIG. 6 is a plot showing the intersection of max dp/dt with the baseline of reflected wave.

The maximum dp/dt of the $P_b$ is then calculated, and the intersection of the upstroke to maximum dp/dt with the baseline of the $P_b$ (see FIG. 6). This determines the initial estimate of the start of the reflected wave ($T_i$).

The pressure values before $T_i$ equal are then made equal to the baseline pressure in $P_b$. A new estimate of both $P_b$ and $P_f$ ($P_{b1}$ and $P_{f1}$) is then calculated as follows.

$P_{b1}(0 \ldots T_i)=P_b(0)$ $P_{f1}(0 \ldots T_i)=P_f(0 \ldots T_i)+(P_b(0 \ldots T_i)-P_{b1}(0 \ldots T_i))$ $P_{b1}(T_i+T_s \ldots T)=P_b(T_i+T_s \ldots T)$ $P_{f1}(T_i+T_s \ldots T)=P_f(T_i+T_s \ldots T)$ where $T_s$=sampling period and T=cardiac period.

A new estimate of the forward wave ($P_{f2}$) is then calculated by smoothing the peak of the wave to ED using spline interpolation. Accordingly, a new estimate of $P_b$ ($P_{b2}$) will be calculated using the following equation.

$P_{b2}(T_{peak} \ldots ED)=P_{b1}(T_{peak} \ldots ED)+(P_{f1}(T_{peak} \ldots ED)-P_{f2}(T_{peak} \ldots ED))$ where $T_{peak}$=Time at the peak of the forward wave.

Figure 7:
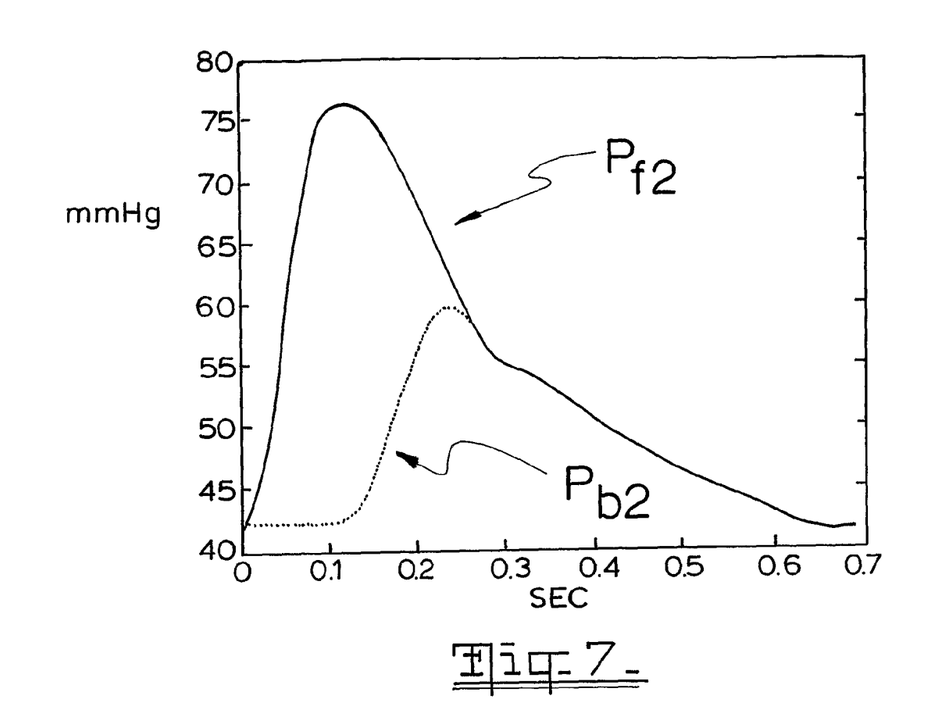
FIG. 7 is a plot of smooth forward and backward waveforms.

The result provides smoother waveforms (see FIG. 7).

Figure 8:
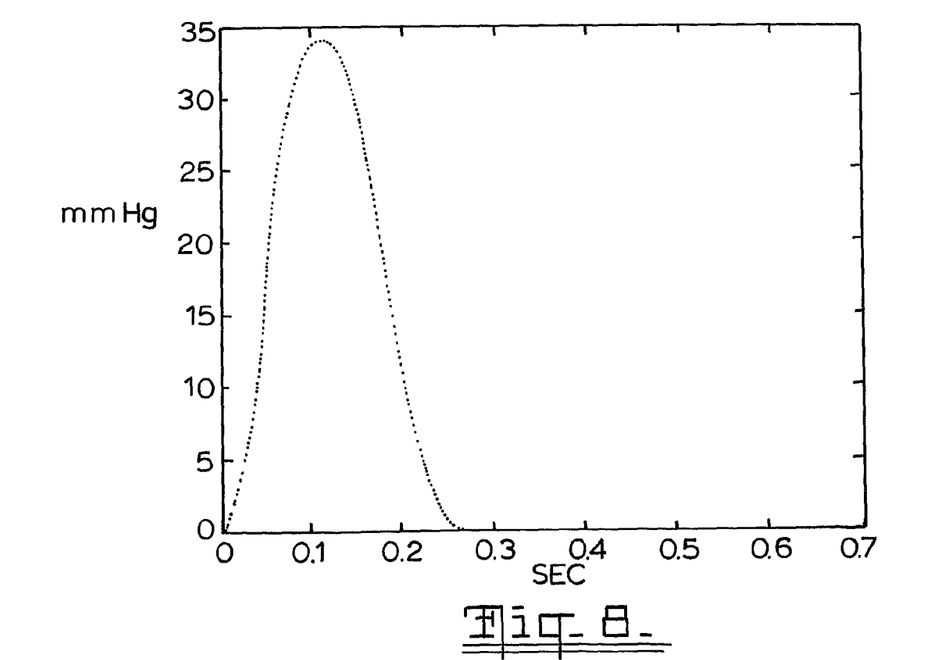
FIG. 8 is a plot of flow waveform calculated from $P_f2$ and $P_b2$.

Calculating the flow from $P_{b2}$ and $P_{f2}$ using the following equation yields a more round flow ($FL_{imp}$) (see FIG. 8)

If any pressure value of $P_{b2}$ before ED is less than the baseline pressure then $T_1$ is reduced by one sampling point and repeat all steps are reflected. If not, continue to the next step.

Figure 9:
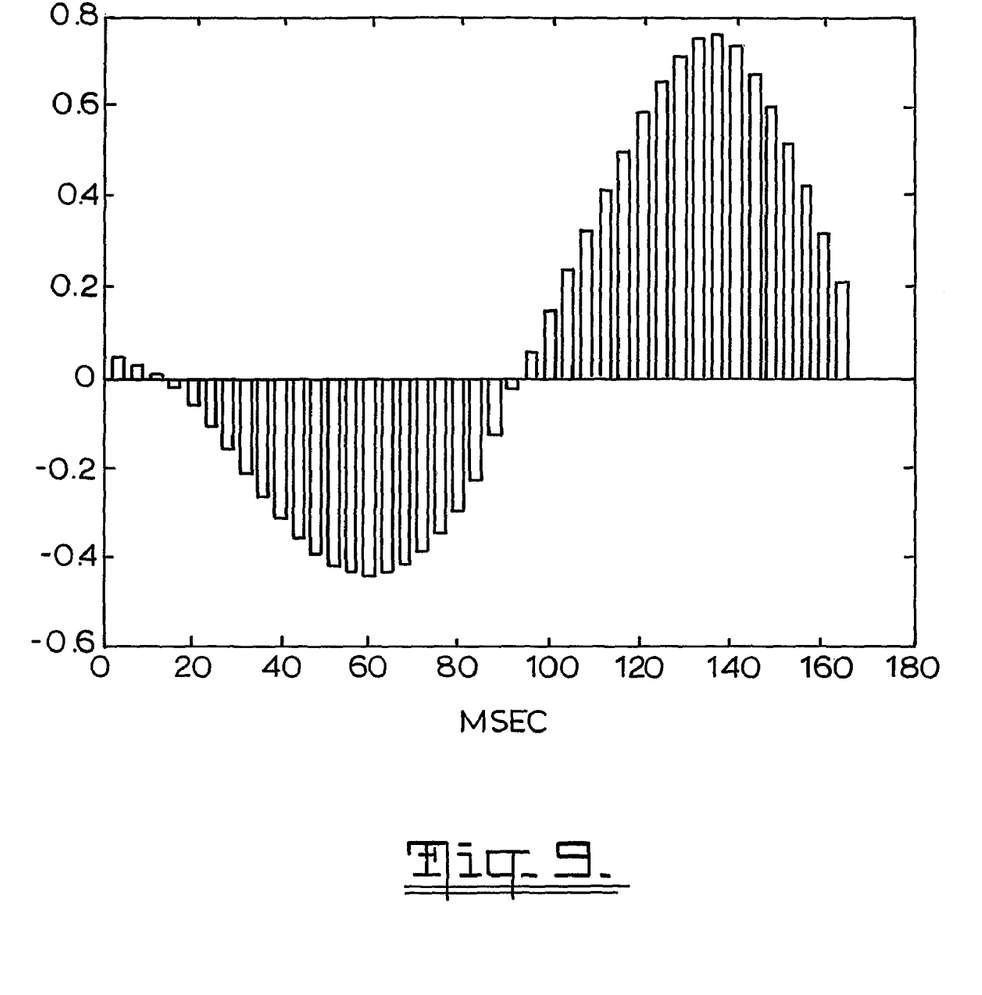
FIG. 9 is a cross-correlation of $P_f2$ and $P_b2$.

$P_{b2}$ and $P_{f2}$ are then re-calibrated so both have the same height and a cross correlation (FIG. 9) is calculated. The time of the highest correlation is the estimated PPTT which is related to transit time in the aorta.

The estimated PPTT is converted to carotid-femoral PPTT using a linear regression equation estimated from analysis of database containing SphygmoCor Pulse Wave Velocity and SphygmoCor Pulse Wave Analysis measurements for the same patients at the same time).

The carotid to femoral arterial distance is estimated by external physiological measurements (eg. with the tape measure 30), or estimated from height, weight and body mass index data.

The PWV is then determined by dividing the carotid to femoral distance by the carotid femoral PPTT The main advantages of the embodiment described is aortic PWV is calculated from only a single central waveform, and with a procedure that is non-invasive to the patient.

The invention claimed is:

1. A method of estimating blood pressure Pulse Wave Velocity (PWV) in the aorta from a recording of a pressure waveform at a single site, the method comprising the following steps:
    (a) measuring a patient's arterial pressure relative to time in order to estimate a central pressure waveform (CPW) at a single site;
    (b) estimating the patient's aortic pressure pulse transit time (PPTT) from the CPW at least by estimating an incident pressure waveform (IPW) and reflected pressure waveform (RPW) components of the patient's CPW, whereby the PPTT has a linear relationship with a time difference between the foot of the IPW and the foot of the RPW;
    (c) estimating the patient's carotid to femoral arterial distance from the patient's physical characteristics; and
    (d) dividing the patient's estimated carotid to femoral arterial distance by the patient's estimated PPTT to estimate the patient's PWV.

2. The method as claimed in claim 1, wherein the patient's single site pressure measurement is taken non-invasively.

3. The method as claimed in claim 1, wherein the patient's radial artery pressure is measured, which is then used to derive the patient's CPW.

4. The method as claimed in claim 1, wherein the patient's carotid artery pressure is measured and used as an approximation of the patient's CPW.

5. The method as claimed in claim 1, wherein the patient's carotid to femoral arterial distance is estimated from the patient's height, weight and body mass index (BMI).

6. The method as claimed in claim 1, wherein the patient's carotid to femoral arterial distance is estimated from a direct measurement of the distance between the carotid and femoral artery.

7. The method as claimed in claim 1, wherein the patient's carotid to femoral arterial distance is estimated from superficial body surface measurements.

8. The method as claimed in claim 1, wherein the aortic PPTT, and both the IPW and RPW components, are calculated non-invasively from an ascending aortic CPW.

9. The method as claimed in claim 8, wherein, to decompose the CPW into the IPW and RPW components, a triangular flow waveform (FL) is estimated from zero at the time of the foot of the wave up to the first systolic peak (T1) in the CPW, which corresponds to the time of peak flow, and then back to zero at the time of the closure of the aortic valve, which is estimated as the ejection duration (ED) from the CPW.

10. The method as claimed in claim 9, wherein the Characteristic Impedance (Zc) is then calculated using the ratio of the Fast Fourier Transform (FFT) of both the CPW and the estimated triangular flow waveform (FL), the characteristic impedance (Zc) then being used derive the IPW and RPW components, based upon an arterial wave reflection model which utilises CPW, Zc and the estimated triangular flow waveform (FL) as input parameters.

11. The method as claimed in claim 10, wherein the estimated triangular flow waveform (FL) is improved by imposing three conditions: the RPW is constant until at least T1; there is no reflection in the IPW after T1; and the RPW from T1 to ED is smoothed using spline interpolation.

12. The method as claimed in claim 11, wherein the patient's estimated PPTT is then calculated using the time between the foot of the IPW and the RPW.

13. The method as claimed in claim 11, wherein estimating the PPTT from the CPW comprises calculating the PPTT using a cross correlation of IPW and RPW.

14. The method as claimed in claim 12, wherein a regression equation is used to convert the patient's estimated PPTT into representing the carotid-femoral transit time, based on analysis of a database containing pulse wave velocity and pulse wave analysis measurements for other the same patients at the same time.

15. The method as claimed in claim 14, wherein the patient's carotid to femoral PWV is then calculated by dividing the patient's carotid to femoral arterial distance by the carotid to femoral transit time.

16. The method as claimed in claim 1, wherein the carotid to femoral PWV is calculated from the IPW and RPW components of the patient's CPW using the following steps:

(e) measuring the time from the foot of the CPW to a first systolic peak (T1);

(f) measuring the time from the foot of the CPW to the closure of the aortic valve, which represents the ejection duration (ED);

(g) estimating a triangular flow waveform (FL) assuming zero flow at the foot of IPW, peak flow at T1 and zero flow again at ED;

(h) calculating a Fast Fourier Transform (FFT) of both the CPW and the estimated triangular flow waveform (FL) to determine the impendence magnitude (Z) using the following formula: Z=FFT(CPW)/FFT(FL);

(i) calculating the characteristic impedance Zc as the average of the $4^{th}$ to $7^{th}$ harmonics;

(j) calculating an IPW (forward) pressure waveform function ($P_f(t)$) using the following equation:

$$P_f(t)=[CPW(t)+ZcFl(t)]/2;$$

(k) calculating an RPW (backward) pressure waveform function ($P_b(t)$) using the following equation:

$$P_b(t)=[CPW(t)-ZcFl(t)]/2;$$

(l) calculating a max dp/dt of $P_b(t)$ and locating an intersection of an upstroke slope with a baseline, the baseline corresponding to $P_b(t=0)$, to initially estimate a start ($T_i$) of a reflected pressure waveform;

(m) making pressure values before $T_i$ equal to the baseline pressure in $P_b$ and calculating a new estimate of $P_b$ and $P_f$ ($P_{b1}$ and $P_{f1}$) using the following formulas:

$$P_{b1}(0\ldots T_i)=P_b(0)$$

$$P_{b1}(T_i+T_s\ldots T)=P_b(T_i+T_s\ldots T)$$

$$P_{f1}(0\ldots T_i)=P_f(0\ldots T_i)+(P_b(0\ldots T_i)-P_{b1}(0\ldots T_i))$$

$$P_{f1}(T_i+T_s\ldots T)=P_f(T_i+T_s\ldots T)$$

where $T_s$=sampling period and T=cardiac period;

(n) calculating a new estimate of the IPW (forward) pressure waveform function ($P_{f2}$) by smoothing a peak of $P_f(t)$ to ED using spline interpolation;

(o) calculating a new estimate of $P_b(t)$ ($P_{b2}$) using the following equation:

$$P_{b2}(T_{peak}\ldots ED)=P_{b1}(T_{peak}\ldots ED\ldots+ (P_{f1}(T_{peak}\ldots ED)-P_{f2}(T_{peak}\ldots ED))$$

where $T_{peak}$=Time at the peak of the forward wave;

(p) calculating an improved estimated flow waveform ($FL_{imp}$) from $P_{b2}$ and $P_{f2}$ using the following equation:

$$FL_{imp}=(2\times P_{f2})-CPW=(2\times P_{b2})+CPW$$

(q) if any pressure value of $P_{b2}$ before ED is less than the baseline pressure then reduce $T_1$ by one sampling point and repeat steps (g) to (p); If not continue to the next step;

(r) re-calibrating $P_{b2}$ and $P_{f2}$ so both have the same height and calculating a cross correlation, wherein the time of the highest correlation represents the aortic PPTT;

(s) converting the estimated PPTT to carotid femoral PPTT using a linear regression equation, based on analysis of a database containing pulse wave velocity and pulse wave analysis measurements for other patients;

(t) calculating the carotid to femoral distance from direct external measurement, or automatically from height and weight or BMI;

(u) determining the carotid-femoral PWV by dividing the carotid to femoral distance by the carotid to femoral PPTT.

* * * * *

UNITED STATES PATENT AND TRADEMARK OFFICE
CERTIFICATE OF CORRECTION

PATENT NO. : 8,273,030 B2  
APPLICATION NO. : 12/095898  
DATED : September 25, 2012  
INVENTOR(S) : Harpas et al.

Page 1 of 1

It is certified that error appears in the above-identified patent and that said Letters Patent is hereby corrected as shown below:

IN THE CLAIMS:

In Column 10, Line 27, in Claim 16, delete "ED))" and insert -- ED))) --, therefor.

In Column 10, Line 31, in Claim 16, delete "CPW" and insert -- CPW; --, therefor.

Signed and Sealed this
Twenty-fourth Day of February, 2015

Michelle K. Lee
*Deputy Director of the United States Patent and Trademark Office*